Figure 2:
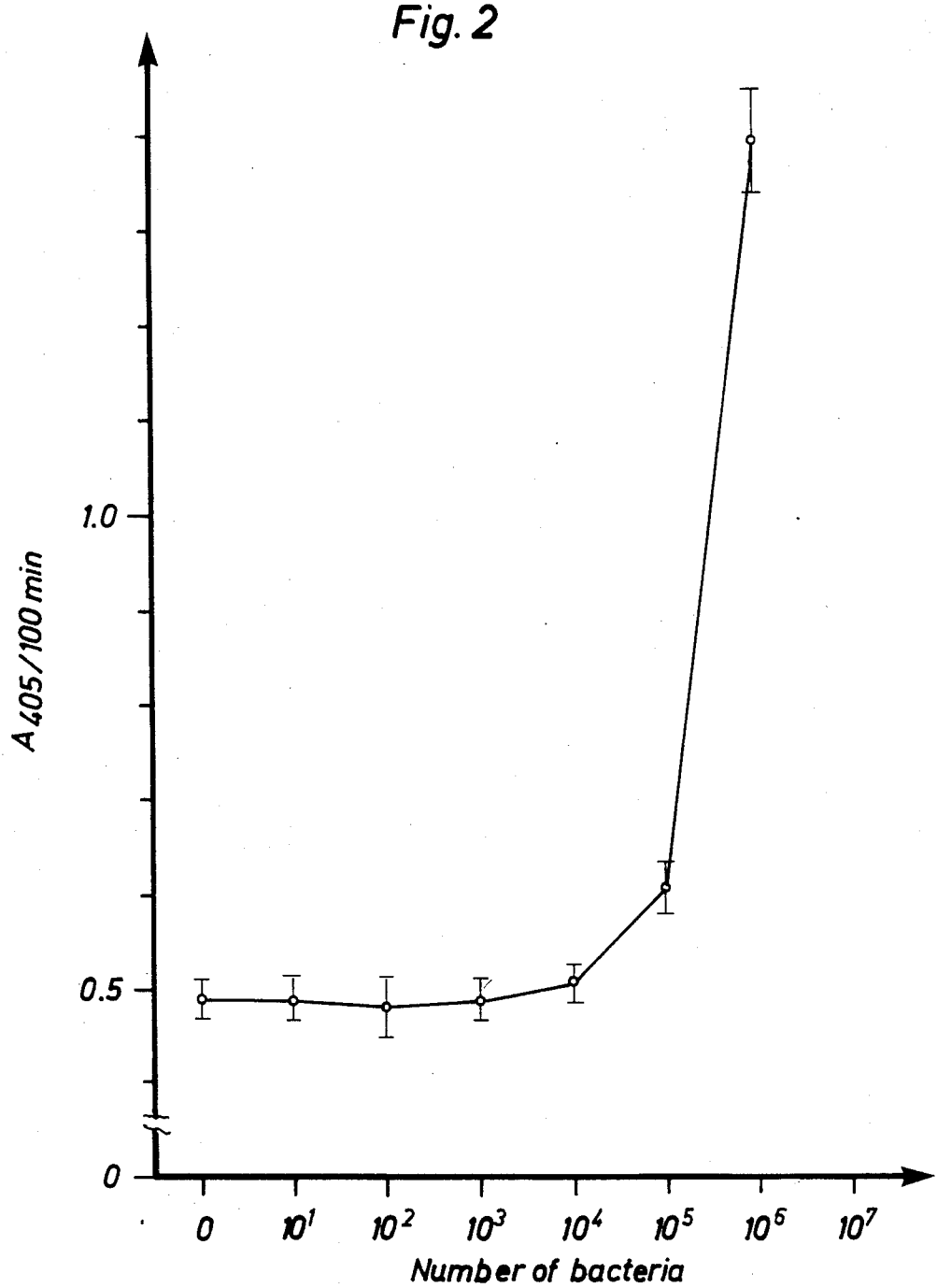

United States Patent [19]

Sandström et al.

[11] Patent Number: 4,822,732
[45] Date of Patent: Apr. 18, 1989

[54] METHOD OF CONCENTRATING AND DETECTING BIOMOLECULES AND CELLS

[75] Inventors: Gunnar Sandström, Sávar; Hans Wolf-Watz, Umeå; Tänavik Arne, Umeå, all of Sweden

[73] Assignee: Symbicom AB, Umeå; Sweden
[21] Appl. No.: 779,775
[22] PCT Filed: Jan. 23, 1985
[86] PCT No.: PCT/SE85/00026
§ 371 Date: Sep. 23, 1985
§ 102(e) Date: Sep. 23, 1985
[87] PCT Pub. No.: WO85/03355
PCT Pub. Date: Aug. 1, 1985

[30] Foreign Application Priority Data

Jan. 24, 1984 [SE] Sweden .............................. 8400374

[51] Int. Cl.$^4$ ................. G01N 33/543; G01N 33/569
[52] U.S. Cl. ......................................... 435/6; 435/7; 436/501; 436/518; 436/531; 436/807
[58] Field of Search ............... 436/807, 531, 501, 518; 435/6, 7

[56] References Cited

U.S. PATENT DOCUMENTS 3,950,134 4/1976 Miles ............................... 436/807 X
4,153,675 5/1979 Kleinerman ..................... 436/807 X
4,693,985 9/1987 Degen ................................. 436/531

FOREIGN PATENT DOCUMENTS 0046004 6/1981 European Pat. Off. .
0144162A2 6/1985 European Pat. Off. .
WOX
8204264 12/1982 PCT Int'l Appl. .
1460631 1/1977 United Kingdom .
1597345 9/1981 United Kingdom .
WOX
8301119 3/1983 World Int. Prop. O. .

OTHER PUBLICATIONS

"Molecular Cell Biology" by James Darnell et al., pp. 643–646, Scientific American Books, W. H. Freeman and Company, New York, 1986.
Australian Patent Abstract, AV-A-90139/82, "Acetylcholine Receptors or Antibodies or Anti-Antibodies Bound to Carrier".
Gochman, N. et al., Anal. Chem., vol. 49, No. 13, 1183A–1187A (1977).
Chemical Abstracts, 91:189319d (1979).

Primary Examiner—Sidney Marantz

[57] ABSTRACT

A method of detecting biological substances having affinity properties by passing the substance to be detected in a flow over a solid surface to which surface a second substance, to which the substance to be detected shows affinity, is attached, so that the two substances form a complex and give enrichment of the substance to be detected. The enrichment is obtained when the fluid volume passing the active surface is many times larger than the volume in contact with the active surface. A means for detecting biological substances consisting of a flow of a fluid sample of the substance to be detected generated via a pump over a solid surface to which another substance, to which the first substance to be detected shows affinity, is attached, so that a complex is formed of the two substances and gives enrichment of the substance to be detected.

8 Claims, 6 Drawing Sheets

Fig. 1

Duct (3)

Pump (2)

Recirculating or waste sample (1)

Y  Antibodies against F. tularensis

◯ Bacteria

Y*  Antibodies labelled with alkaline phosphatase

Reading

METHOD OF CONCENTRATING AND DETECTING BIOMOLECULES AND CELLS

This invention relates to a method and a means for concentrating and detecting biological material.

Previously known methods for assaying biological and biochemical materials have been unsatisfactory as it has often been difficult to concentrate said material for assay. Different techniques, such as spin-drying and ultrafiltration, to obtain an increased concentration of the biological and biochemical material to be analysed have been used. However, it appeared that several molecules could not be concentrated in such a way and examples thereof are antigens, nucleic acids, hormones, enzymes, ligands, etc. A serious drawback with said techniques is that also contaminating molecules are concentrated and interfere with the detection of the desired material.

The present invention relates to a method for separately concentrating biological and biochemical materials having affinity properties. This is achieved by letting, in a flow, a fluid sample of the material to be detected and which material has affinity to another material, such as antigen-antibody, DNA-DNA, DNA-RNA, RNA-RNA, lectin-receptor, receptor-ligand as well as other bio-specific pairs, e.g. phages and viruses, pass a solid surface, at which surface the other material to which the material to be detected has affinity is attached, so that in relation to the volume of the fluid a many times larger volume passes the surface. During the passage of the flow, the material to be detected adheres to the other material to which it has affinity and forms a complex, which can be read off by different markers such as enzymes, radio activity, laser, etc.

The detection process according to this invention can be automatized and the sensitivity increased at least ten times as compared to previously known methods such as "enzyme-linked immunosorbent assay" (ELISA) with microplates or by radioimmunoanalysis (RIA) techniques, immunofluorescence, etc. (Voller, A., Bartlett, A., and Bidwell, D. E., "Enzyme immunoassays with special reference to ELISA techniques", *J. Clin. Pathol.* 31, 507–520 (1978); Overby, L. R., and Mushahwar, J. K., "Radioimmune assays", p. 39–70, in M. W. Rytel (Ed.), Rapid diagnosis in infectious disease, CRC Press, Boca, Fla. (1979); Dahle, A. B., and Laake, M., "Diversity dynamics of marine bacteria studies by immunofluorescent staining on membrane filter", *Appl. Environ. Microbiol.* 43, 169–176 (1982).

Depending on the flow ratio and the flow time, a considerable lower limit for the detectable level is obtained. The concentration of bacteria and the amounts of the bound substances are other variables. The extent of bound substance is increased with increased specificity.

The amount of flow must be tested each time and depends inter alia on the size of the molecules to be detected.

The solid surface can be any solid surface which is immobilized, but is preferably hydrophobic and consists of polymeric substances such as glass, plastic material, metal, silicon, etc. The binding to said surface is obtained (1) by passive adsorption to the hydrophobic surface, or (2) by immobilizing the specific molecule, e.g. antibody, enzyme, antigen, to a solid phase by adsorption or covalent binding.

The fluid sample can consist of water, water-based systems, e.g. buffer, body fluids, in cyclon media impacted air samples, in suitable buffer systems re-suspended solid samples containing the substance to be detected.

In bacteria assay it has been shown to be advantageous if the sample contains at least $10^3$ bacteria per milliliter suspended therein, but also as small amounts as $10^2$ bacteria per milliliter could be detected.

The concentration of the desired substance can be decreased if the volume of the sample is increased and yet give detectable results.

A non-limiting example of a means used according to the present invention is shown in the enclosed schematical view of the concentration process by means of immunological technique (FIG. 1).

A sample (1) containing for example antigen is pumped by a pump (2) into a duct (3) to the inner surfaces of which antibodies are bound. By the flow through the duct antigens are deposited on the antibodies and form a complex which is read off by different markers, e.g. a colour reaction with alkaline phosphatases.

Hitherto used assay methods such as the above mentioned ELISA-methods have restrictions as regards the lowest amounts of detectable antigen (sensitivity). Different direct concentration increasing measures such as centrifugation and ultrafiltration have, as stated above, been used to increase the concentration and sensitivity without giving satisfactory results.

Antibodies obtained from rabbits which had obtained antigens from *Francisella tularensis* (the causative agent of tularemia) were tested regarding their ability to recognize whole bacteria of *F. tularensis*. It was then found that the antibodies were bound to the surfaces of the bacteria and could be used as a diagnostic means. An assay system was developed based on said antibodies in which the marker antibodies were affinity purified against the antigens and labelled with alkaline phophatase.

When said diagnostic system was tested with whole bacteria of *F. tularensis* by so-called microplate-ELISA, it was found that the lowest amount of bacteria that significantly could be detected by said method was at a concentration of $10^5$ bacteria per milliliter (FIG. 2).

Concentration by centrifugation or ultrafiltration gave the same result on analysis (i.e. no increase was obtained, not shown).

Investigations of epidemics of tularemia have shown that *F. tularensis* can be present in and spread by water and air. A demand for assay of water and air containing minor amounts of bacteria has thus arisen. Another existing demand is also to assay very small samples, such as body fluids.

As mentioned above, the ELISA-methods as used proved to be unsatisfactory, as the lowest amounts of bacteria that can be detected by said methods are within a concentration of $10^5$ bacteria per milliliter.

Therefore, tests were made using the affinity of *F. tularensis* to specified antibodies to increase the sensitivity of the test.

A surface antigen was prepared as described by Sandström, G., Tärnvik, A., Wolf-Watz, H., and Lofgren, S., "Preparation of antigen from *Francisella tularensis* for demonstration of antibodies by the ELISA", FOA Report C 40179-B 3, June 1983, Unea, Sweden.

A surface antigen (Sandström et al., Inf. Imm. 45, 101–106 (1984) was isolated which immunized on rabbit gave specific antibodies against *F. tularensis* (Sandström, G., and Wolf-Watz, H., "Rapid identification of *Francisella tularensis* in water", FOA Report C 40188-B 3, November 1983, Umea, Sweden.

Rabbit sera

Rabbits were immunized by *F. tularensis* antigen as described by Sandström, G., and Wolf-Watz, H., "Rapid identification of *Francisella tularensis* in water", FOA Report C 40188-B 3, November 1983, Umea, Sweden.

Affinity purification and alkaline phosphatase-coupling to rabbit antibodies A live vaccine strain of *F. tularensis* (*F. tularensis* LVS) was provided by the U.S. Army Medical Research Institute of Infectious Diseases, Fort Detrick, Frederick, Md., USA. A wild strain of *F. tularensis* var. palaerctica (strain SBL R45) was provided by R. Möllby, The National Swedish Bacteriological Laboratory, Stockholm, Sweden.

Bacteria of two strains of *F. tularensis* were grown on modified Thayer-Martin agar containing Gc-medium base (36 grams/liter; Difco Laboratories, Detroit, Mich., USA), hemoglobin (10 grams/liter; Difco) and IsoVitalex (10 milligrams/liter; BBL Microbiology Systems, Cockeysville, Md., USA) at 37° C. in 5% $CO_2$ in air. The bacteria population was determined by counting live bacteria.

Fluid test

Tap water was adjusted to pH 5.0 using 0.01M hydrochloric acid. Tween ® 20 was added to each sample at a concentration of 0.05% (v/v). *F. tularensis* bacteria were suspended in amounts of 0, $10^1$, $10^2$, $10^3$, $10^4$ and $10^5$/ml, respectively, or alternatively, cyclon medium was supplemented with 0.05% (v/v) Tween ® 20 (Olsson, T., Stymne, S., and Thore, A., "Detektion av bakterieaerosoler med luminescensanalys 1. Luminescensanalys av luftprover", FOA Report C 40061-B 2 (1977), Ursvik, Sweden.

REFERENCE EXAMPLE

Antigen - antibody

Microplate ELISA was performed substantially according to Voller, et al., "Enzyme immuno assays with special reference to ELISA techniques", *J. Clin. Pathol.*, 31, 507–520 (1978). Rabbit antiserum against *F. tularensis*-antigen diluted 100:1 (ELISA-titer 1:5000) in 0.05M sodium bicarbonate buffer pH 9.6 was coated on microplates (Flow Laboratories Svenska AB, Stockholm, Sweden). Bacterial suspensions were added to the microplates which were incubated for one hour at 37° C. In the next step, a solution of affinity-purified, alkaline phosphatase labelled rabbit antibodies against *F. tularensis* antigen was applied for one hour at 37° C. The reaction developed by the addition of the substrate to the enzyme and the absorbance at 405 nm was measured. The results thus obtained are shown in FIG. 2 and Table 2.

EXAMPLE

Antigen - antibody

The process was performed in plastic tubes (Tygon ®; Noax AB, Stockholm, Sweden) connected to a peristaltic pump system (Technicon Corp., Ardesly, U.S.A.). The volume of the tube was 40 µl/cm tube. For each assay 10 cm of tube was connected. Antiserum in a stationary condition was coated over night at room temperature. Test samples were passed through the tube at a flow rate of 1.9 ml/min. (FIG. 3).

In some experiments test samples were stationary in the tube while during other tests a flow was generated through the tube.

After washing, stationary exposure to alkaline phosphatase-labelled antibodies was performed at 37° C.for one hour. The tubes were disconnected from the pump system and cut from each side to a length of 5 cm, and substrate to alkaline phosphatase was added. After incubation at 37° C.for 30 minutes the content of each tube (200 µl) was transferred to the well of a microplate and the absorbance at 405 nm was measured. The samples were tested in triplicate and the mean values were calculated.

Figure 3:
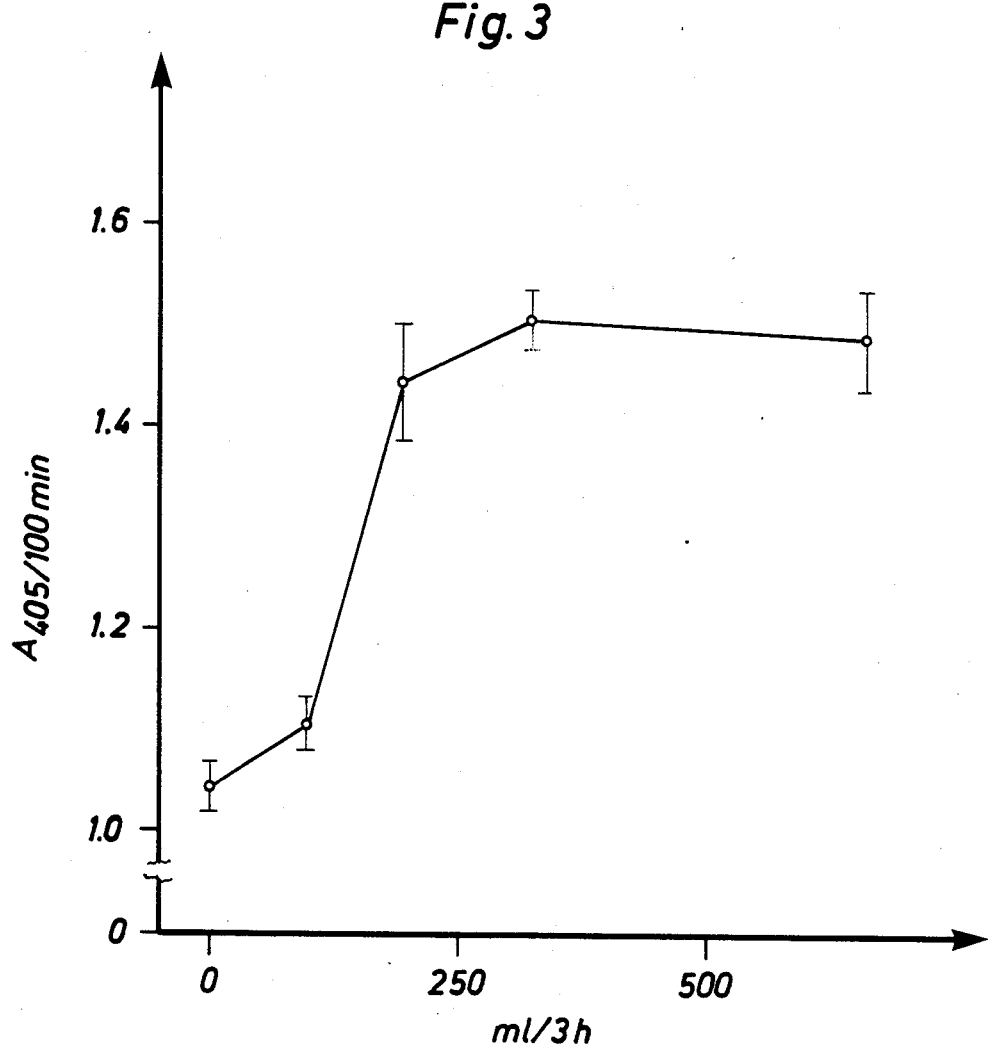

When the test samples were stationary in the duct, lower ELISA values were obtained in relation to the values obtained when the samples were flown through the duct (FIG. 3).

Figure 4:
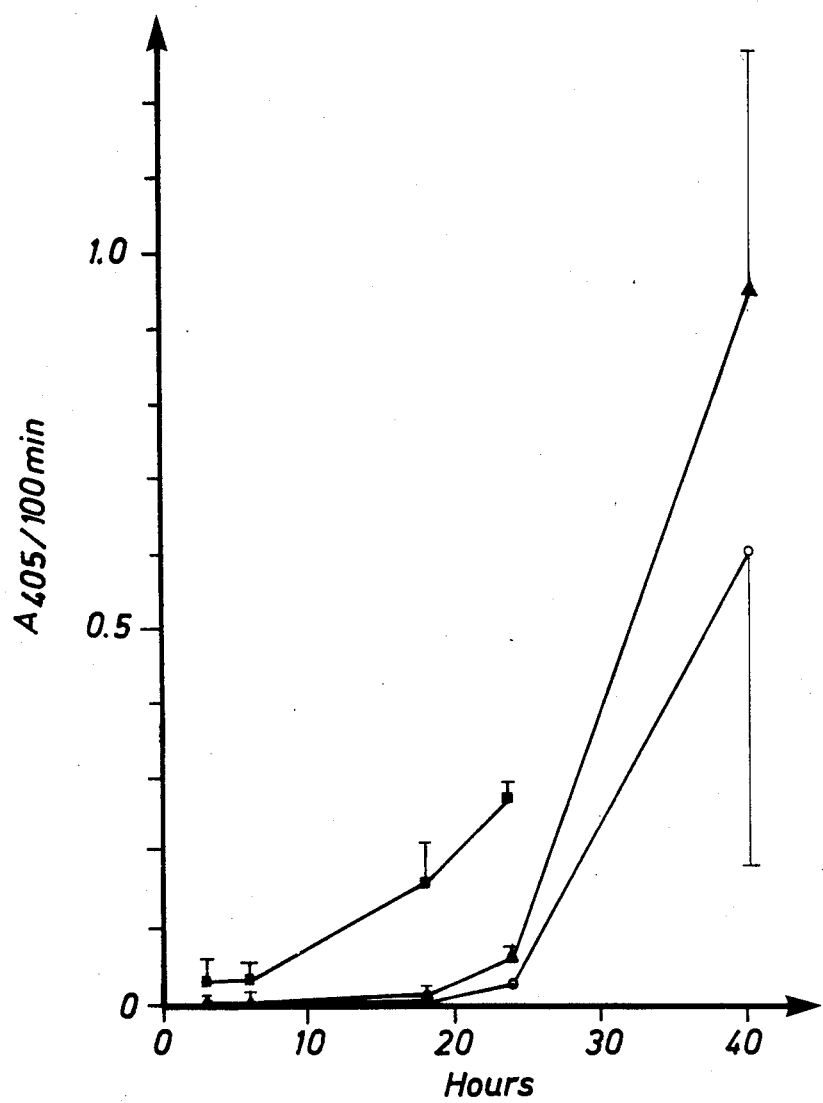

By using the process according to the present invention, an increased sensitivity was obtained. With an unlimited test sample it is possible to detect as few as $10^2$ *F. tularensis* per milliliter (FIG. 4). Viable counts of *F. tularensis* before and after the passage through the duct did not show any measurable decrease in bacteria.

The possibilities of recirculating different volumes of test samples containing *F. tularensis* were tested. The smallest volume that for practical reasons could be recirculated was a 5 ml test sample. The sensitivity ws increased at least 10 times (FIG. 5), generally between 10–100 times, in relation to the time during which the test sample was recirculated (FIG. 4). By circulating $10^4$ *F. tularensis* bacteria suspended in 5, 15, and 50 ml of fluid test samples for 18 hours increased values were obtained depending on the amounts of fluid sample as tested (Table 1).

When different volumes of the sample containing *F. tularensis* were flown through the duct coated with antibodies specific against *F. tularensis,* an enrichment in bacteria in the duct was obtained. When larger volumes were passed through the duct, a plateau level was obtained (FIG. 3), probably due to the fact that all antigen deposition sites were already occupied and thus no further bacteria could be trapped.

Similar results were obtained when *F. tularensis* were impacted in cyclon media supplemented with 0.05% (v/v) Tween ® 20 (Olsson, T., Stymne, S., and Thore, A., "Detektion av bakterieaerosoler med luminescensanalys 1. Luminescensanalys av luftprover", FOA Report C 40061-B 2 (1977), Ursvik, Sweden.

Receptor-ligand-interaction

*E. coli* (HB101/pRHU845) agglutinates A blood via mannose-resistant hemagglutination. Interaction occurs between a special protein structure of the bacteria to a Gal-NAc $\beta$ (1→3) Gal 2 (1→4) Gal $\beta$ (1→4) GLC-ceramide receptor on red blood corpuscles.

A plastic tube (Tygon ®) was coated with whole blood (A-blood). *E. coli* bacteria in concentrations of from 0 to $5.10^6$ bacteria per milliliter were flooded through the tube system. Thereafter rabbit antibodies against *E. coli* were added. Then anti-rabbit IgG labelled with alkaline phosphatase were added for one hour at 37° C. and finally the absorbance at 405 nm was monitored by the addition of substrate to alkaline phosphatase. Using this method it was possible to detect *E. coli* at different densities.

TABLE 1

Results obtained when $10^4$ *F. tularensis* were circulated in varying amounts of fluid test sample for 18 hours.

| Volume[a] (ml) | A 405/100 minutes | |
|---|---|---|
| | 0 *F. tul*/ml | $10^4$ *F. tul*/ml |
| 5 | 0.57 ± 0.06 | 0.87 ± 0.13 |
| 15 | 0.60 ± 0.07 | 1.13 ± 0.20 |
| 50 | 0.68 ± 0.05 | 1.27 ± 0.23 |

[a]Recirculated for 18 hours
A405/100 min. = absorbance at 405 nm/100 min.

The results are mean values of 3 measurements.

TABLE 2

Results obtained for tests using microplate ELISA, assay with the fluid stationary in the duct and assay with a flow

| Amount of bacteria per ml | Microplate ELISA | Fluid stationary in the duct (Tygon ® plastic tube) | Fluid in flow (Tygon ® plastic tube) |
|---|---|---|---|
| $10^5$ | 0.125[a] | 0.335 | 0.504 |
| $10^4$ | 0.028 | 0.086 | 0.162 |
| $10^3$ | 0.000 | 0.027 | 0.064 |

[a]Absorbance at 405 nm/100 min. The values are decreased by the values obtained for tap water without *F. tularensis*.

The level of detectable *F. tularensis* LVS was increased by using the fluid in flow. Suspensions containing $10^3$, $10^4$ and $10^5$ *F. tularensis* cells per milliliter were passed through a Tygon ® plastic tube coated with antibodies against *F. tularensis*. The flow rate of the test suspension was about 100 ml per 3 hours. According to this process the amount of *F. tularensis* LVS was enriched and the detectable level became lower than the detectable level obtained with microplate ELISA.

The influence of Tygon ® plastic tube was examined. The ELISA assay was performed without any flow in the Tygon ® plastic tube. The advantages of the fluid in flow where shown also in this test. A lower detectable level was obtained as compared to microplate ELISA.

LEGENDS TO FIGURES

FIG. 1: Enrichment of the duct walls using a flow system. The flow rate was 1.9 ml/min. and the volume 40 μl/cm in the duct. The test sample was either flown straight through the duct or recirculated. The assay was performed in the same way as the microplate ELISA assay with respect to antigen and antibody. The length of the duct was 10 cm during the process, except for the last step when enzyme substrate was added. Before said addition the duct was cut from both ends to a length of 5 cm.

FIG. 2: ELISA was performed in microplates. The microplates were pre-coated with immune serum against *F. tularensis* antigen at room temperature over night. The test samples were added after washing and allowed to react at 37° C. for one hour. Affinity purified anti-*F. tularensis* antibodies labelled with alkaline phosphatase were subsequently added and the microplates were incubated for one hour at 37° C. Enzyme substrate was finally added and the reaction monitored after 30 minutes, using an automatic spectrophotometer. Stated values are mean values ± standard deviation of 16 samples.

FIG. 3: Enrichment of *F. tularensis* at the duct wall using different volumes of water containing $10^5$ bacteria per milliliter. The test time was 3 hours. Stated values are mean values ± standard deviation of 3 samples.

FIG. 4: The detection level for different concentrations of *F. tularensis* depended on the volume of the test sample which passed through the pre-coated Tygon( ® ) tube. After 3 hours, $10^4$ *F. tularensis* could be detected.

To obtain a significant detection level for as few as $10^2$ bacteria per milliliter, about 4.5 l sample (a total of $4.510 \times 10^5$ bacteria) was allowed to pass the Tygon ® tube.

Said test shows that antigen can be enriched at the inner wall of the Tygon ® tube if said tube is coated with specific antibodies. It is also evident that the test time, i.e. the enrichment time, depends on the amount of bacteria in the sample to be tested.

| Bacteria/ml | Graph plotting |
|---|---|
| $10^2$ | o—o |
| $10^3$ | ▲—▲ |
| $10^4$ | ■—■ |

Mean values ± standard deviation of 9–12 samples.
The background values (tap water without *F. tularensis*) are subtracted from the values as stated.

Figure 5:
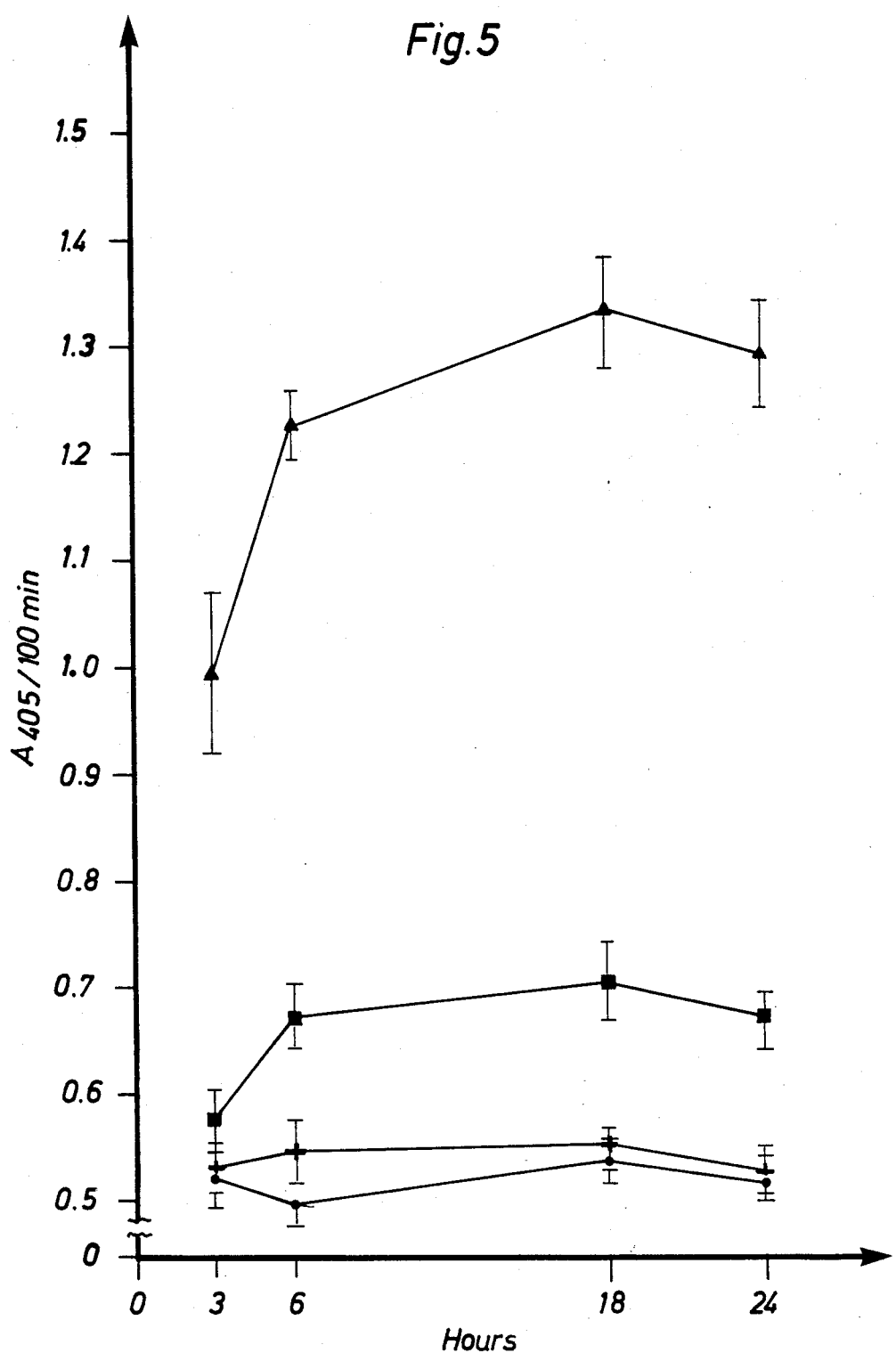

FIG. 5: Detection levels of *F. tularensis* when test samples are recirculated.

| Bacteria/ml | Graph plotting |
|---|---|
| $10^2$ | o—o |
| $10^3$ | +—+ |
| $10^4$ | ■—■ |
| $10^5$ | ▲—▲ |

The measurements were performed after 3, 6, 18 and 24 hours. Stated values are mean values ± standard deviation of 10–15 samples.

Figure 6:
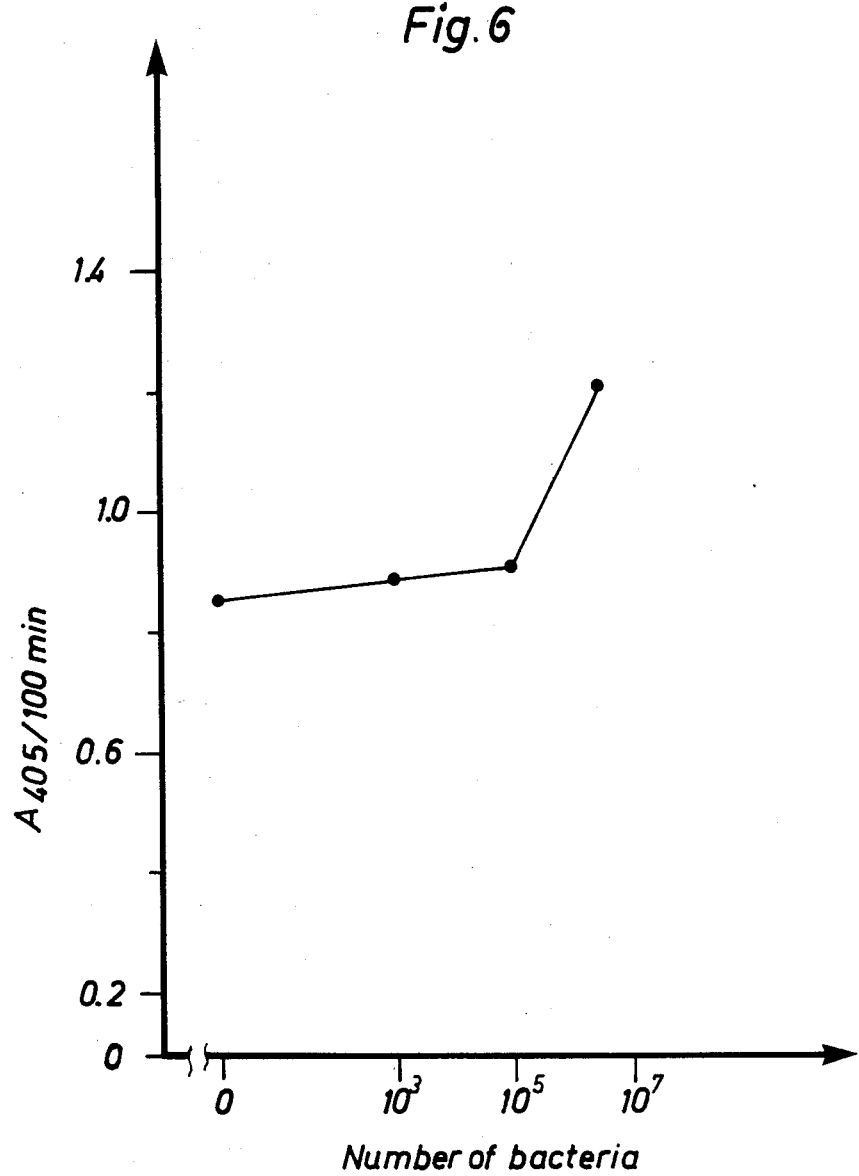

FIG. 6: Absorbance at 405 nm/100 min. at test with *E. coli* in concentrations between 0 and $5.10^6$ per milliliter. The sample was recirculated for 3 hours. Volume=5 milliliter. Stated values are mean values of 3 samples.

We claim:

1. A method of detecting a biological substance in a fluid test sample, comprising the steps of:
   flowing said fluid test sample through a housing having a solid inner peripheral surface to which a second substance, having an affinity for said biological substance, is attached, thereby defining an active surface within said housing, the volume of said fluid which is at any one time upon said active surface being far less than the total volume of said fluid test sample flowed across said active surface.

2. A method according to claim 1 wherein the biological substance and the second substance, or vice-versa combine to form a pair selected from the group consisting of antigen-antibody, DNA-DNA, DNA-RNA, and receptor-ligand other than antigen-antibody.

3. A method according to claim 1, wherein the flow is generated by a pump.

4. A method according to claim 1, wherein the flow without being recirculated passes across the active surface.

5. A method according to claim 1, wherein the flow is recirculated.

6. A method according to claim 1, characterized in that the flow rate is determined with respect to the size of the molecule to be detected.

7. The method of claim 1, wherein said housing is a tube.

8. The method of claim 7, wherein said tube has two open ends.

* * * * *